United States Patent
Schultz

(10) Patent No.: US 10,247,533 B2
(45) Date of Patent: Apr. 2, 2019

(54) ISCHIAL TUBEROSITY MEASUREMENT TOOL

(71) Applicant: Richard Schultz, San Juan Capistrano, CA (US)

(72) Inventor: Richard Schultz, San Juan Capistrano, CA (US)

(*) Notice: Subject to any disclaimer, the term of this patent is extended or adjusted under 35 U.S.C. 154(b) by 225 days.

(21) Appl. No.: 15/210,683

(22) Filed: Jul. 14, 2016

(65) Prior Publication Data

US 2018/0017368 A1 Jan. 18, 2018

(51) Int. Cl.
  *G01B 5/14* (2006.01)
  *A61B 5/107* (2006.01)
(52) U.S. Cl.
  CPC .............. *G01B 5/14* (2013.01); *A61B 5/107* (2013.01)
(58) Field of Classification Search
  CPC ........................................................ G01B 5/14
  USPC ................................................... 33/512, 574
  See application file for complete search history.

(56) References Cited

U.S. PATENT DOCUMENTS

| 7,284,336 B2* | 10/2007 | Bird | B62J 1/002 33/512 |
|---|---|---|---|
| 7,441,343 B2* | 10/2008 | Bird | B62J 1/002 33/512 |
| 2006/0218809 A1* | 10/2006 | Bird | B62J 1/002 33/512 |
| 2007/0057562 A1* | 3/2007 | Gregory | A47C 7/022 297/452.21 |
| 2018/0017368 A1* | 1/2018 | Schultz | A61B 5/107 |

* cited by examiner

*Primary Examiner* — Yaritza Guadalupe

(57) ABSTRACT

A tool which incorporates separated dual-impression pads for measuring the Ischial Tuberosity width of a cyclist more accurately since these dual-impression pads match the newer saddles designs. The accuracy of the measurement is further increased by heavy ferrous balls that indefinitely hold the impressions to give the bike fitter enough time to make an accurate Ischial Tuberosity width measurement. The accuracy of the saddle selection is further increased due to the detachable/portable measurement caliper which can be taken out to the saddles being considered.

8 Claims, 15 Drawing Sheets

ISCHIAL TUBEROSITY MEASUREMENT TOOL

BACKGROUND OF THE INVENTION

1. Field of Invention

Certain embodiments disclosed herein relate to apparatus and methods for fitting a cyclist with a saddle, including a bicycle saddle.

2. Description of the Related Art

Bicycle saddles have traditionally been designed with a complex upper surface (convex—side to side, slightly concave—front to back) on which the cyclist sits. The pressure of these saddles on the perineal area can cause numbness in both male and female cyclists. In some cases, after prolonged riding, a male cyclist can experience Erectile Dysfunction and impotence due to a decrease in blood flow in the pudendal arteries as a result of this pressure. With prolonged periods on their saddle, some women cyclists have had difficulties urinating or sustaining sexual intercourse Recently, saddle manufacturers have greatly improved the bicycle saddle by introducing saddles having a central groove and/or cutout. This cutout minimizes the pressure on the perineal area of the cyclist which attempts to remedy these problems and limit these issues. This IT measuring device is essential to ensure that the cyclists can choose from a selection of the correct saddle for them.

SUMMARY OF THE INVENTION

As with the height of humans. the widths of Ischial Tuberosities (Sit Bones) between individuals also varies. This is the part of the body that first contacts the saddle. Everyone has a different width Ischial Tuberosity and the importance for a cyclist in finding the exact width saddle is critical for long-term health. When the cyclist comes into contact with the bicycle saddle, their weight and support should be with their Ischial Tuberosities (IT). When sitting on the saddle correctly, most of the cyclists' weight should be supported by this bone structure and not on their sensitive soft tissue, pudendal nerves or arteries. As mentioned before, excessive weight on the soft tissue can lead to health issues such as tumors, genital numbness and even erectile dysfunction due to Pudendal nerve compression and or crushing and or blocking of the Pudendal artery.

In one embodiment, a bicycle saddle fitting tool comprises two sit-bone impression regions which simulate having the cyclist being sized to a saddle that has a cutout. Two balls are stored into the fitting tool base. Once the impressions are made by the cyclist, the balls are placed and will self-level into these impressions to show the exact IT width. A detached measurement gauge will then be used to note the exact IT width of the cyclist. The measurement gauge caliper or ruler is usable to measure the saddle which will show both the bike fitter and the cyclist exactly where they will sit on any given saddle, as well as how much drop from the horizontal plane to the exact point of contact the IT will have with the saddle.

In another embodiment, a bicycle saddle fit system comprises a single impression pad of enough length and width to span the sit bones of minor and adult humans. Two balls which will self-level into the depressions of the impression pad will show the cyclists' IT width and a detached measurement gauge will then be used to note the exact IT width of the cyclist. The measurement gauge caliper or ruler is usable to measure the saddle which will show both the bike fitter and the cyclist exactly where they will sit on any given saddle, as well as how much drop from the horizontal plane to the exact point of contact the IT will have with the saddle.

For the purpose of summarizing the invention, certain objects and advantages have been described herein. It is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The apparatus and methods of the invention have been described with some particularity, but the specific designs, constructions, and steps disclosed are not to be taken as delimiting of the invention. A wide range of modifications and alternative structures and steps for practicing the invention will make themselves apparent to those of ordinary skill in the art, all of which will not depart from the essence of the invention, and all such changes and modifications are intended to be encompassed within the appended claims.

DETAILED DESCRIPTION OF THE PREFERRED EMBODIMENT

FIG. 1, FIG. 1a, FIG. 2, FIG. 2a, FIG. 3 depict one embodiment of a saddle fitting tool 100 having dual impression pads. FIG. 1b depicts another embodiment of a saddle fitting tool 100 which includes a single impression pad. The saddle fitting tool 100 is usable to fit a saddle, preferably a bicycle saddle, to a cyclist by measuring the distance between the Ischial Tuberosities (IT or sit bones) of the cyclists' pelvis.

NOTE: In the embodiment of the IT measurement tool 100 FIG. 1; 110 comprises two impression pads 110a and 110b. In another embodiment of the IT measurement tool 100 FIG. 17 indicates a single impression pad. This differentiation will be used throughout this claim.

Figure 6:
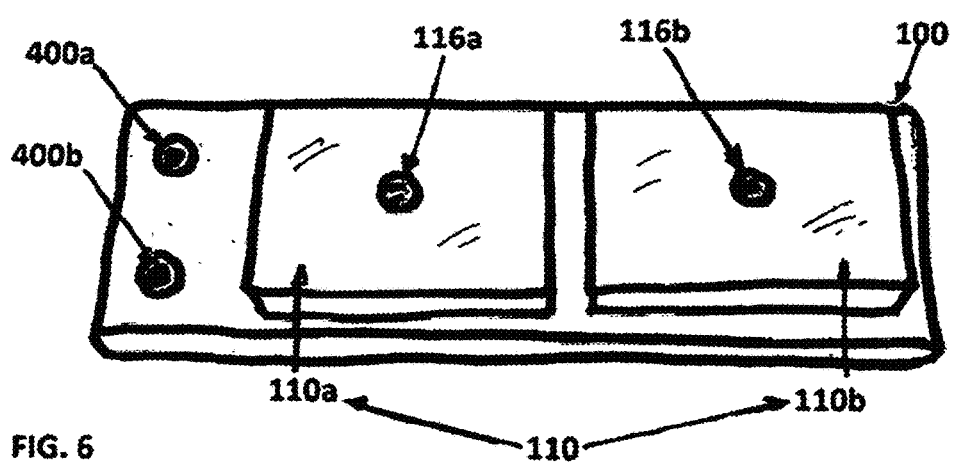
FIG. 6—is a plan view of the saddle fitting tool of FIG. 1, depicting the measurement of IT bone impressions made in the impression pads of the fitting tool.
Figure 8:
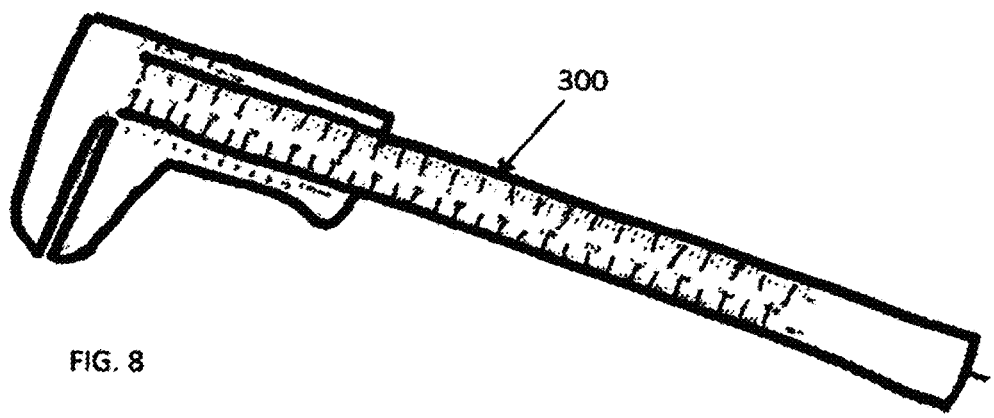
FIG. 8—is a plan view of the caliper IT measuring tool to be used for saddle fitting tool of FIG. 1.
Figure 9:
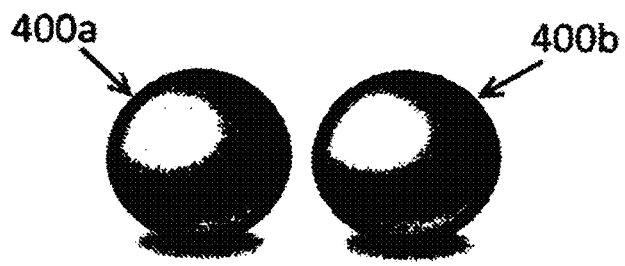
FIG. 9—is a plan view of the two (2) balls that will self-level and find the center of the IT bone impressions left by the seated cyclist on saddle fitting tool of FIG. 1.

The depicted embodiment of the fitting tool 100 generally comprises impression pads 110 which are affixed to and overlies a substrate layer 120. The substrate layer 120 preferably includes an exposed portion 122 which extends laterally beyond the perimeter of the impression pad 110 as a place to hold and/or store the measuring balls as depicted in FIG. 6 and FIG. 9. Ferrous steel measuring balls can be held in place using underside attached magnets as depicted in FIG. 1a. Non-ferrous or non-metallic measuring balls are held in place via gravity. A detached measurement gauge FIG. 8, 300 is part of the fitting system but not attached to the saddle fitting tool 100.

Figure 1:
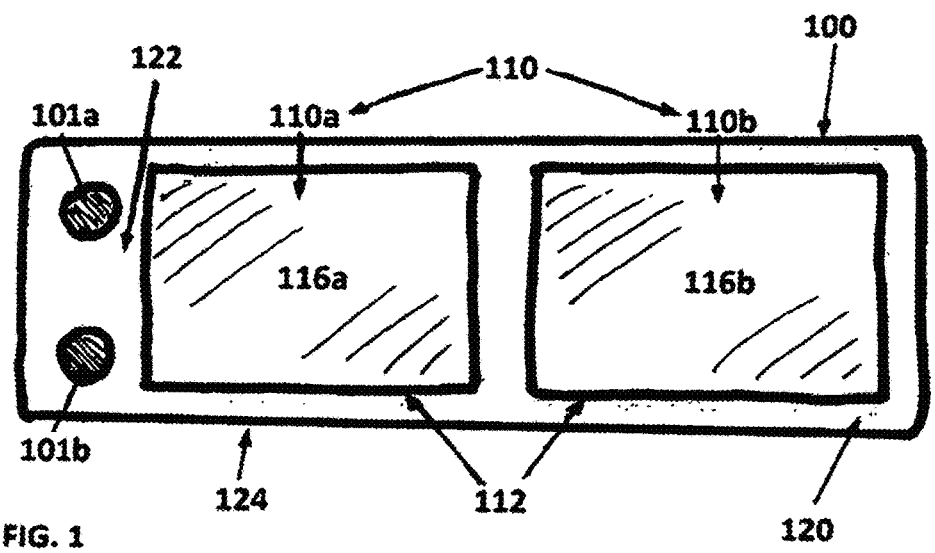
FIG. 1—is a plan view of one embodiment of a saddle fitting tool utilizing dual impression pads.
Figure 1A:
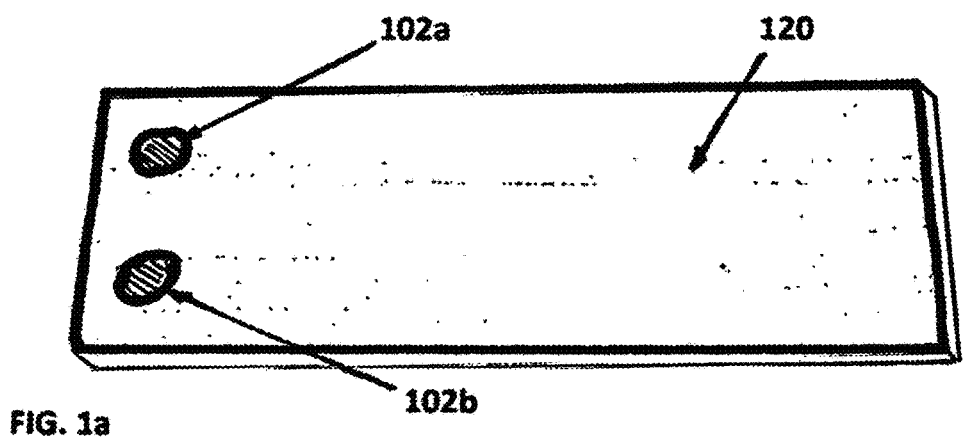
FIG. 1a—is a plan view of the underside of one embodiment of a saddle fitting tool.
Figure 1B:
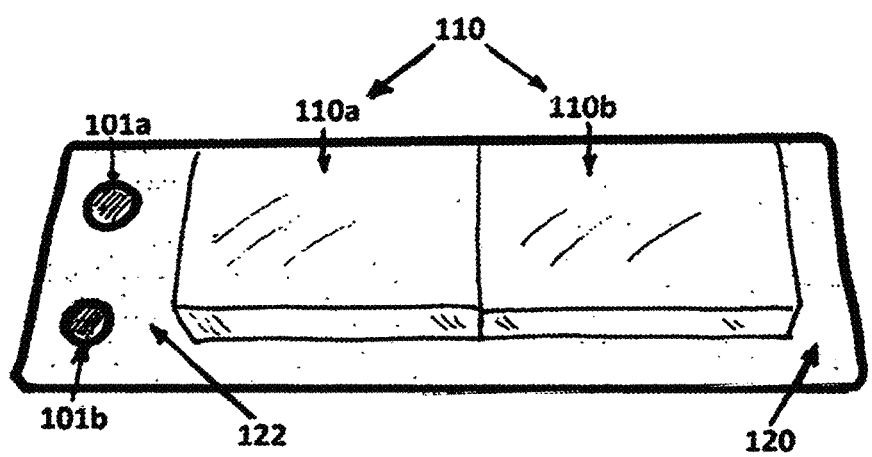
FIG. 1b—is another plan view of an embodiment of a saddle fitting tool utilizing a single impression pad.
Figure 2:
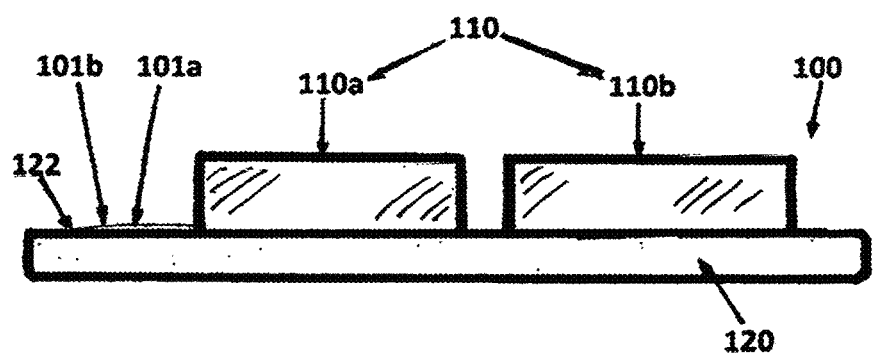
FIG. 2—is an elevation view of the saddle fitting tool of FIG. 1.
Figure 2A:
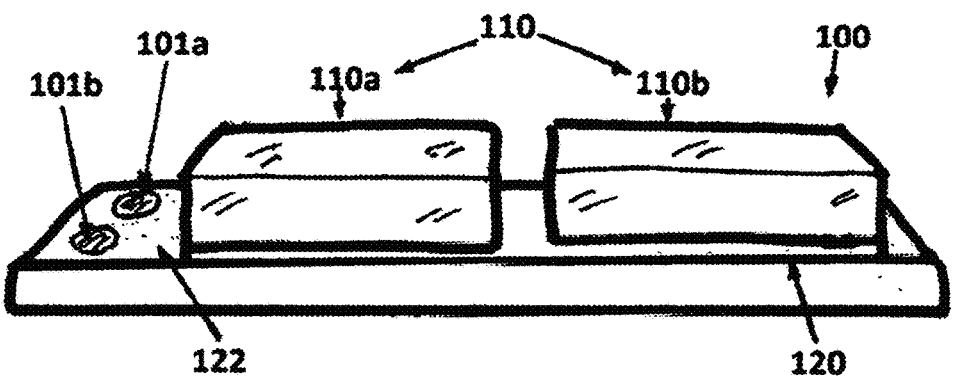
FIG. 2a—is an elevation perspective view of the saddle fitting tool of FIG. 1
Figure 3:
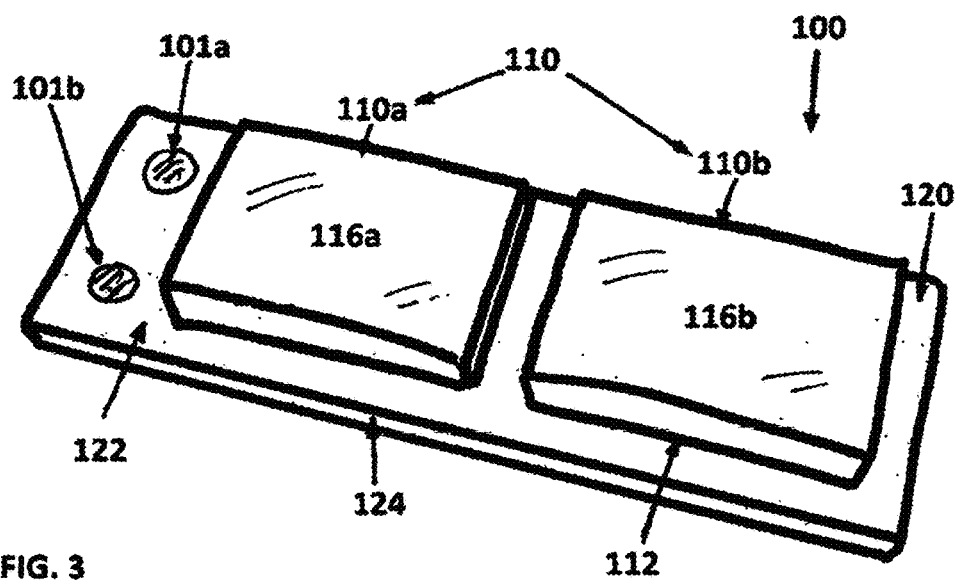
FIG. 3—is a perspective view of the saddle fitting tool of FIG. 1.

The impression pad 110 preferably comprises dual-pieces of shape-memory material, FIG. 1, 110a, 110b, such as foam, foam rubber, memory foam, or alternatively cardboard or clay. Alternatively, a single piece of shape-memory material such as foam, foam rubber, memory foam can also be used in lieu of dual pieces FIG. 1b, FIG. 17, 110. This measuring tool will work in either configuration. Generally, the impression pad 110 can comprise any material that is sufficiently compressible to form, at least temporarily, impressions of the sit bones of an adult or juvenile cyclist recently seated on the impression pad. Where the impression pad 110 is formed from a material which forms such impressions only temporarily, the material preferably has sufficient shape memory to maintain the impressions long enough to permit the measurement of a distance between the impressions as further discussed below. Such an impression pad 110 can therefore be configured to hold the impressions for at least 5 seconds, or at least 10 seconds, or greater than 10 seconds in various embodiments. Using heavy ferrous steel balls FIG. 9 have an advantage since the weight of the balls as they sit on the impression pad(s) will maintain the impressions much longer allowing ample time for the fitter to more accurately measure the IT width of the cyclist. Using this method with a reusable impression pad such as memory foam facilitates repeated measurements with the same impression pad allowing a cyclist to take multiple measurements of IT bone width and average the measurements for improved accuracy. The impression pads 110a, 110b, 110 can therefore be configured to hold the impressions for various lengths of time, in various embodiments.

In dual-pad embodiment, the impression pads 110a, 110b are each adequately large to span each IT bone width of a large adult cyclists' pelvis. These impression pads will also measure the IT bone width of a juvenile cyclist.

Figure 7:
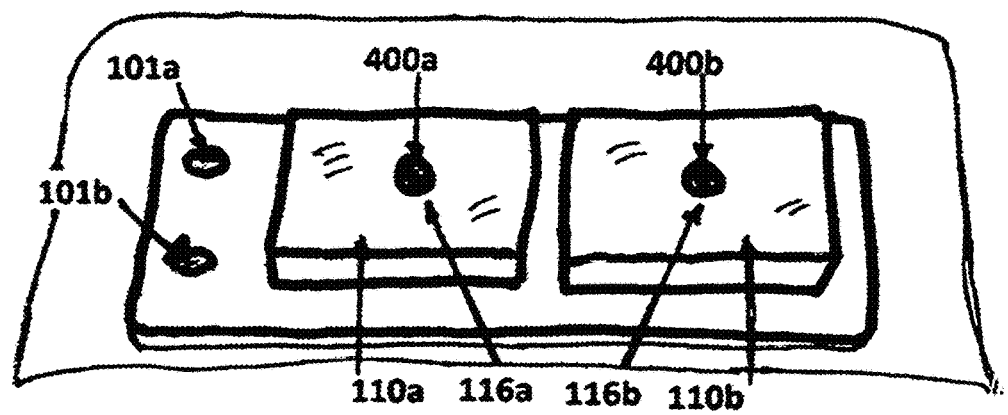
FIG. 7—is a plan view of the saddle fitting tool of FIG. 1, depicting the measurement of IT bone impressions after setting self-leveling balls onto the indentations of the impression pad of the fitting tool.

Alternatively, a single impression pad may be employed, for example in a fitting tool 100 intended for a slightly easier and quicker IT and saddle fitting experience for the cyclist FIG. 1b, FIG. 7.

The size of the Impression pad(s) 110, 110a, 110b is preferably selected to include additional area beyond the largest IT bone width that the pad(s) 110, 110a, 110b is intended to accommodate.

In the depicted embodiment, the impression pads 110a, 110b are a single layer of memory foam, each about 101 mm (4 inches) wide with a maximum depth of about 101 mm (4 inches) and a thickness of about 28 mm (1.1 inches). While these are only preferred dimensions, they may be varied as is appropriate.

In various embodiments, dual or single impression pad design, the width of the impression pad(s) 110, 110a, 110b can be about 150-610 mm (6 inches-24 inches). The depth of the impression pad 110 can be about 50-460 mm (2 inches-18 inches while the thickness of the impression pad 110 can be about 2.5-105 mm (0.1 inches-4 inches). As depicted in FIG. 1, this bicycle saddle fit system tool can be used for either adult, juvenile or child cyclist emphasizing a fitting for a bicycle saddle with a slit or hole in the center.

The perimeter 112 FIG. 1 of the impression pads 110a, 110b can have any suitable shape; however, in the depicted embodiment the perimeter 112 has a shape approximating that of two rectangles, one for the left side IT bone and one for the right side IT bone. This dual-sided impression pad advantageously assists the cyclist in centering the impression pad before they sit on it. A different embodiment is depicted as 110 in FIG. 17, defining a single, larger rectangle, one that is large enough to accommodate both IT bones The substrate layer 120 preferably comprises a relatively stiff layer of wood. Alternatively, other relatively stiff materials may be used to construct the substrate layer 120. These can be rubber, plastic, fiberglass, carbon fiber or any other organic or inorganic stiff material in which impression pad(s) can be mounted.

Figure 10:
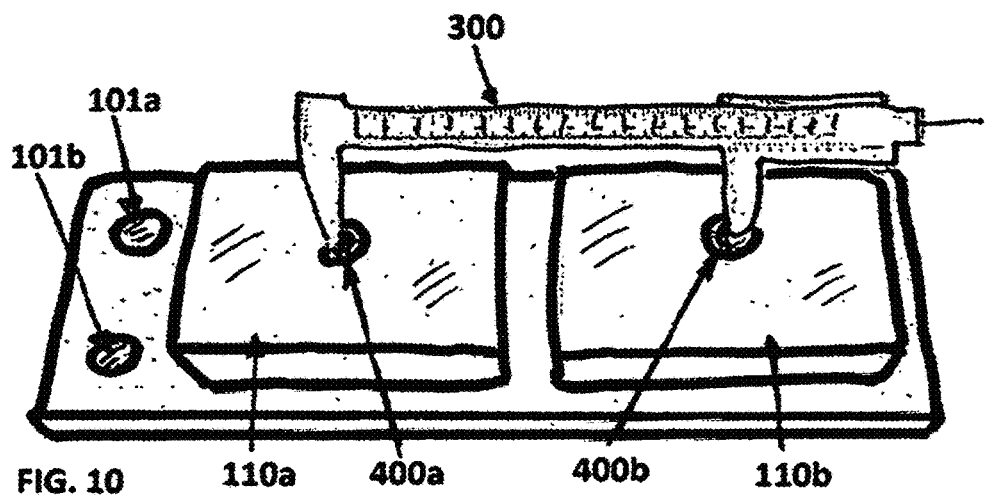
FIG. 10—is a plan view of the caliper IT bone measuring tool in use for saddle fitting tool of FIG. 1.

As mentioned above, the measuring tool 100 includes a detached measurement gauge 300 FIG. 8, that, in conjunction with self-centering balls 400a, 400b FIG. 9 are used to measure the exact IT bone width. The depicted measurement gauge 300 has an adjustable sliding measuring scale that, when closed, measures zero point and when slid open as depicted in FIG. 10, the measuring tips are used to measure the distance between the center points of each ball by physically placing the edge of each point onto the center of each ball 400a, 400b. This arrangement of the balls 400a, 400b, used in conjunction with the detached measuring gauge 300 facilitates easy and accurate measurement of IT bone width. The measuring gauge 300 can be denominated with millimeters as shown, or with centimeters, inches, or any other suitable measurement unit.

Figure 4:
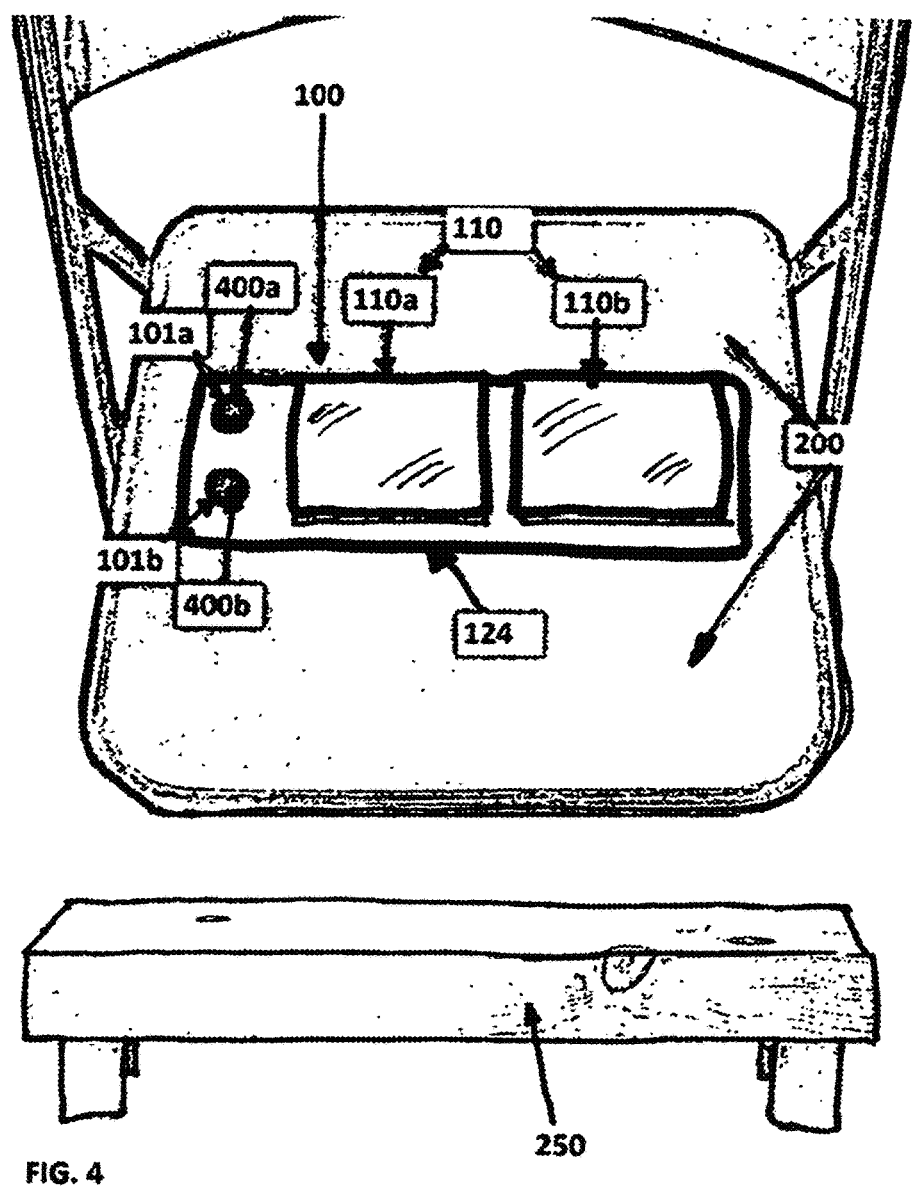
FIG. 4—is a plan view of the saddle fitting tool of FIG. 1, as situated on a chair for use accompanied by a plan view of a step for the cyclists' feet.
Figure 5:
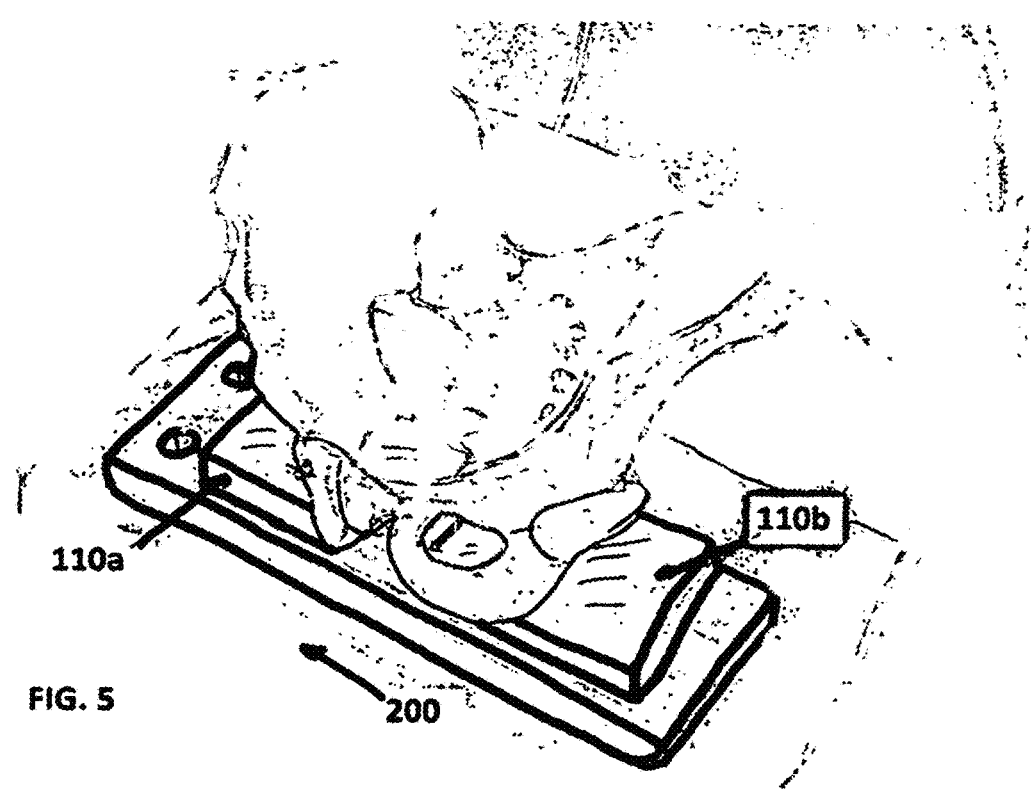
FIG. 5—is a plan view of the saddle fitting tool of FIG. 1, in use to measure the IT bone width of a cyclist.
Figure 5A:
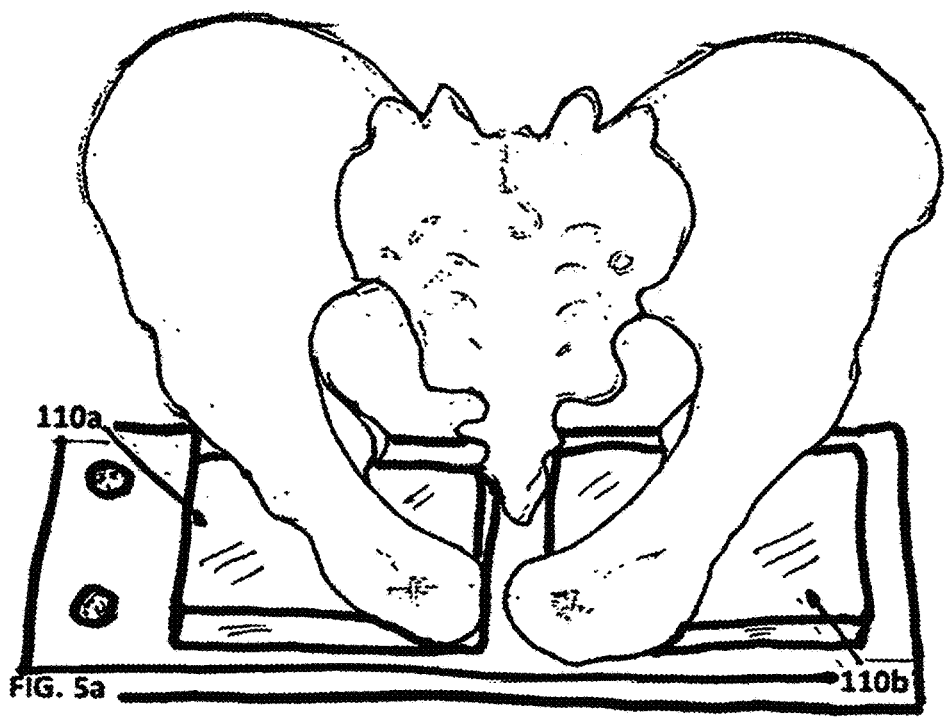
FIG. 5a—is a zoomed-in close-up plan view of the saddle fitting tool of FIG. 1, in use to measure the IT bone width of a cyclist.
Figure 17:
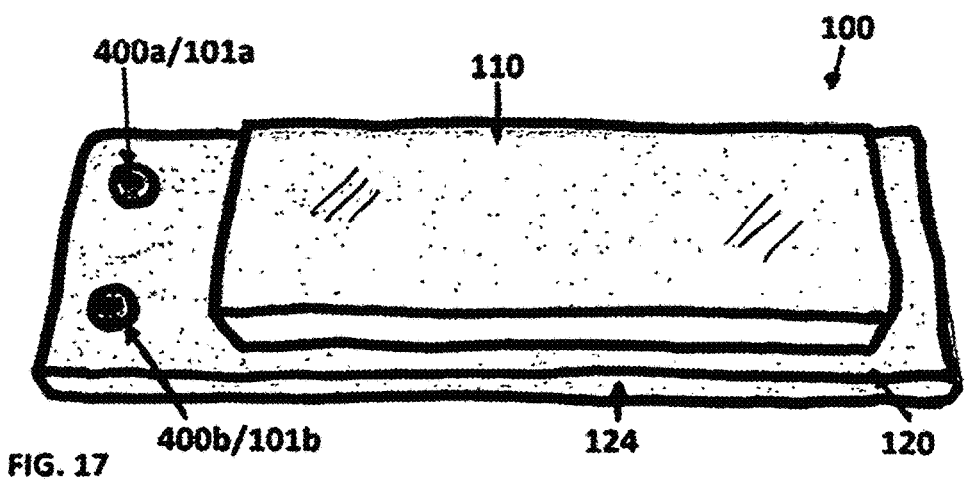
FIG. 17—is a plan view of another embodiment of a saddle fitting tool.

FIGS. 4-7 depict an embodiment of a method of fitting a saddle to a cyclist. FIG. 17 depicts another embodiment of a method of fitting a saddle to a cyclist. The various embodiments of fitting methods described herein may be performed with any of the embodiments of the fitting tool 100 described herein, or with any other suitable fitting tool.
How to Measure the it Bones of the Cyclist A cyclist sits on the impression pads 110a, 110b (see FIG. 1, FIG. 5, FIG. 5a.) in a manner that both of the cyclist's IT bones push into and against the impression pads 110a, 110b. As seen in FIG. 4, FIG. 5, FIG. 5a, the cyclist preferably sits on the impression pads 110a, 110b in a slightly forward-leaning posture, and/or with the knees slightly raised so that there is a greater force pressing the IT bones into the impression pad. This will place the greatest force on the IT bones allowing a deeper depression 116a, 116b FIG. 6 in the impression pads 110a, 110b. Other knee/hip configurations and angles may be employed by the cyclist and fitter. A foot support 250 FIG. 4 may be provided to support the feet of the cyclist to easier facilitate the raised-knee posture of FIG. 5, FIG. 5a.

Figure 6A:
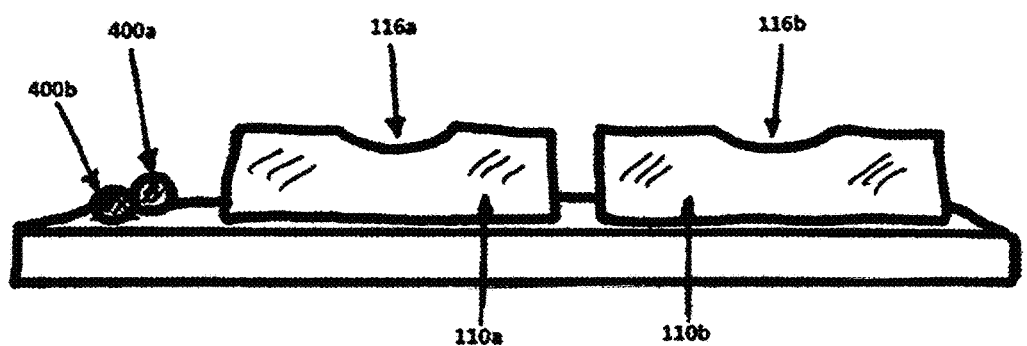
FIG. 6a—is an elevation view of the saddle fitting tool of FIG. 1, depicting a 'cut away' view of the impressions made in the impression pads of the fitting tool.

The IT bones of the seated cyclist create IT bone impressions 116a, 116b, FIG. 6, FIG. 6a in the impression pads 110a, 110b FIG. 6, FIG. 6a. After the cyclist has stood up from the impression pads 110a, 110b, FIG. 6, FIG. 6a, the distance between the IT bones can be measured by taking the 2 supplied balls 400a, 400b FIG. 6, FIG. 6a, FIG. 7, FIG. 9, from the balls holder 101a, 101b FIG. 1, FIG. 7 and then placing the balls 400a, 400b into the depressions 116a, 116b, FIG. 6, FIG. 6a, FIG. 7 left by the previously seated cyclist. The balls will self-level 400a, 400b FIG. 7 to the center of the IT bone depressions 116a, 116b, FIG. 6, FIG. 6a where detached supplied measuring tool 300, FIG. 8, FIG. 10 will be used to measure the distance between the two balls 400a, 400b, FIG. 10 which will be the exact measurement—center-to-center of the cyclists' IT bone width. Alternatively, since the diameter of the balls 400a, 400b FIG. 9 resemble the width of the cyclists' actual IT bones, the distance between the outer edge of 440a to the outer edge of 400b FIG. 10 can also be used to determine IT bone width and ultimately the correct saddle width size. As previously stated, since the impression foam can be used repeatedly, several measurements can be taken where the final width is determined by averaging the multiple and independent measurements. This leads to an even greater accuracy for the cyclists' IT width.

In various embodiments, the ball holder(s) 101a, 101b FIG. 1, FIG. 7 can be two single holders configured so that each ball holder holds one ball or can be configured in a single larger ball holder that holds both balls.

Once the cyclists' IT bone width has been measured and recorded on the measuring device 300, FIG. 8, FIG. 10, the correct saddle or correct group of saddles can be down-selected from the vast number of saddles offered for sale via the cyclists' preferred business. It is important to note that most saddles fit into one of two categories 510, 520 FIG. 11 described in further detail below.

Figure 11:
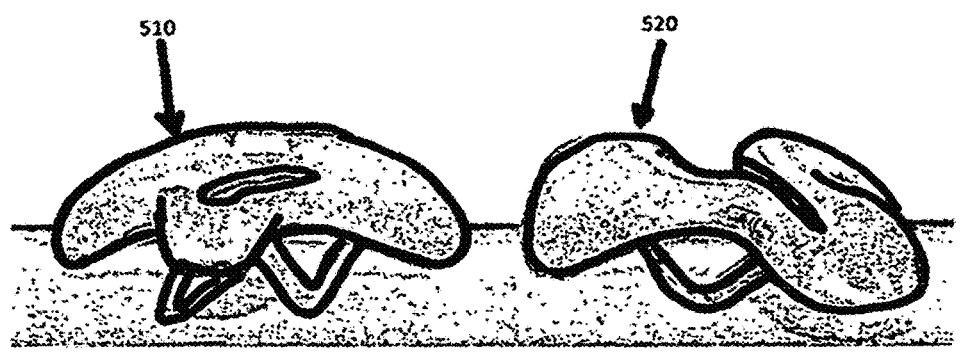
FIG. 11—is an elevation view of two saddles viewed from the front of one embodiment of a group of saddles for use with the saddle fitting tool of FIG. 1.
Figure 12:
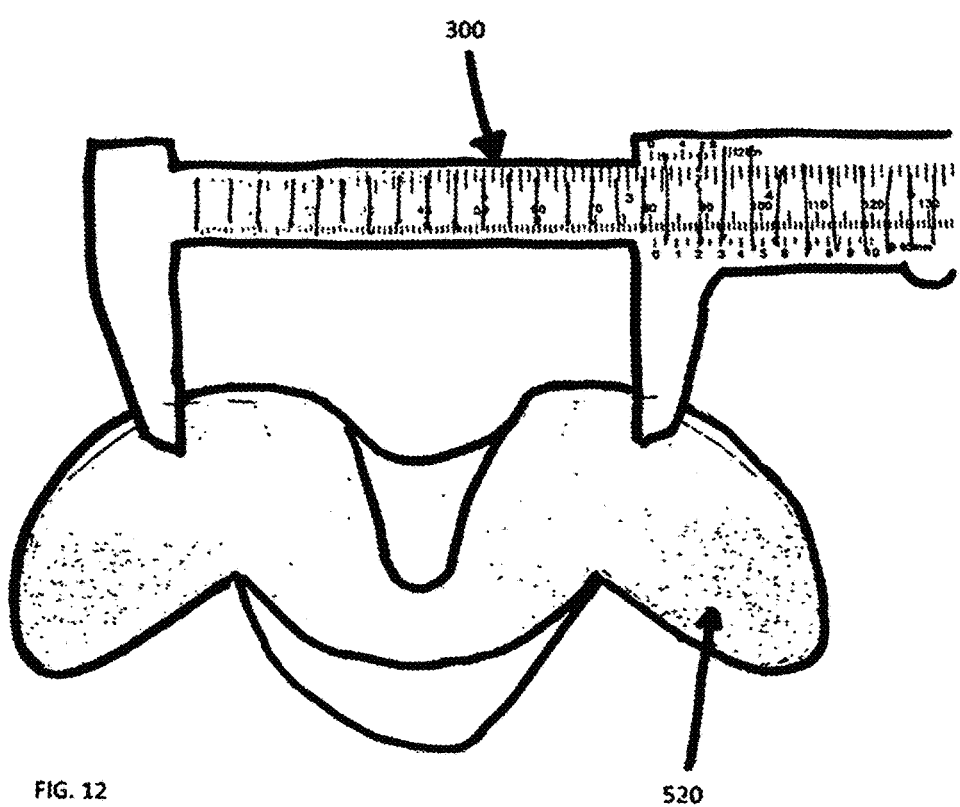
FIG. 12—is an elevation view showing the front of one embodiment of a curved-top saddle showing the caliper gauge IT bone measuring tool set to a specific IT bone width and showing where the cyclists' IT bones will be set on the saddle.
Figure 13:
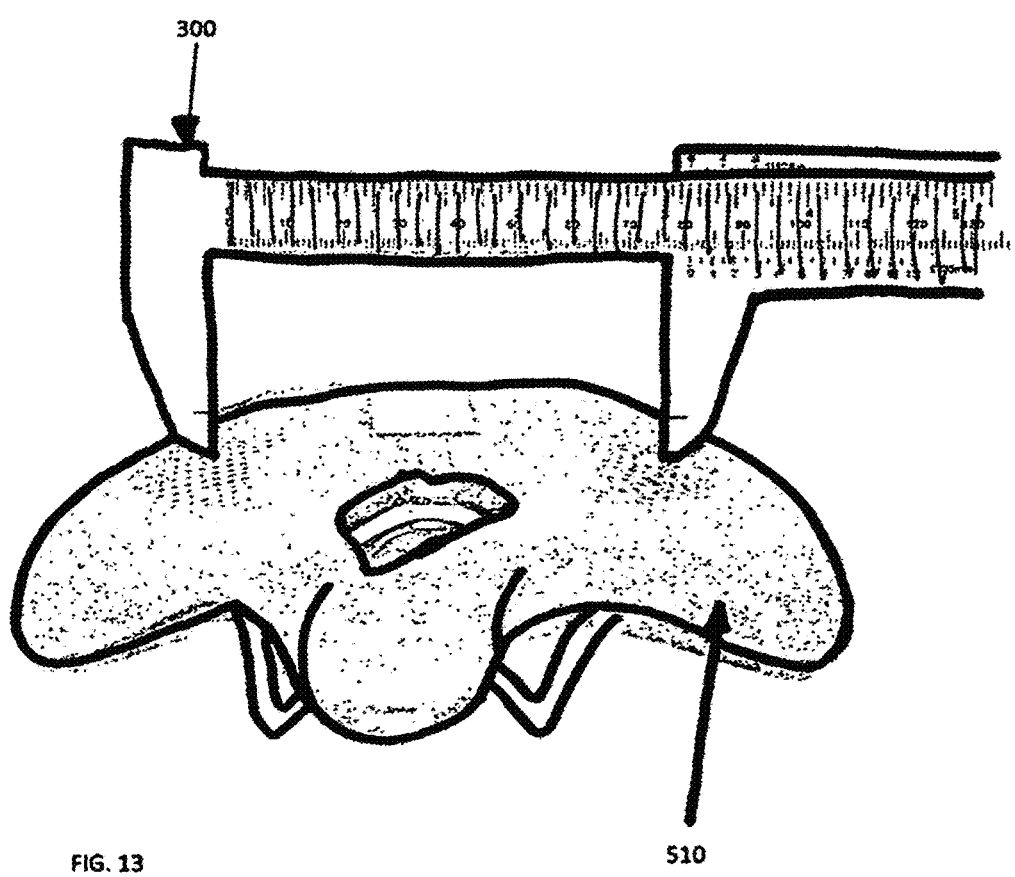
FIG. 13—is an elevation view showing the front of one embodiment of a flat-top saddle showing the caliper gauge IT bone measuring tool set to a specific IT bone width and showing where the cyclists' IT bones will be set on the saddle.
Figure 14:
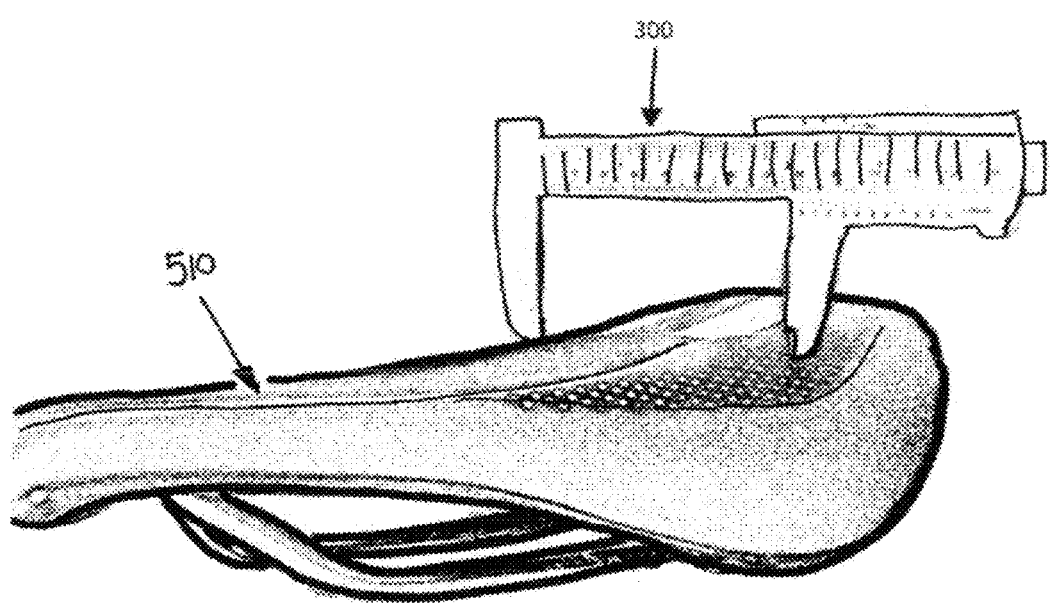
FIG. 14—is a side elevation view of one embodiment of a flat-top saddle showing the caliper gauge IT bone measuring tool set to a specific IT bone width and showing where the cyclists' IT bones will be set on the saddle as depicted in FIG. 13.
Figure 15:
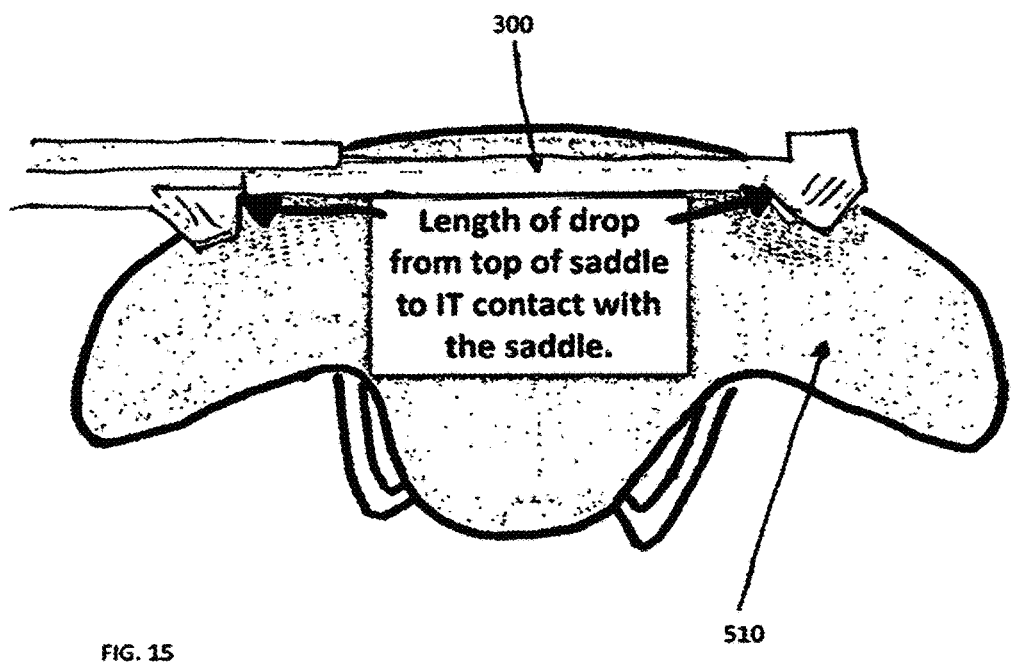
FIG. 15—is a front elevation view of one embodiment of a flat-top saddle showing the caliper gauge IT bone measuring tool set to measure distance from where the soft tissue sets on the saddle top to how much lower the IT bones sit on the saddle.

510, FIG. 11, FIG. 13, FIG. 15 represents a saddle which is flatter along the top rear where the cyclists' IT bones rest. 520, FIG. 11, FIG. 12, FIG. 14, FIG. 16 represents a saddle with an aggressive slope from the top-middle/top-center to the sides/edges of the saddle. It is a matter of preference that some cyclists' prefer a saddle with a flat-top, while some cyclists' prefer a saddle with more of a curve. A cyclists' preference is mainly dependent upon which is the most comfortable for the cyclist. Some cyclists have larger legs and might prefer the sloped saddle since the saddle does not interfere with or come into contact with the cyclists' legs when pedaling. Other cyclists prefer flat top saddles since this style allows the cyclist to easily move around on the saddle. Since different cyclists prefer differently shaped saddles, of paramount importance is to get the cyclist the correct width saddle.

As stated previously, the most important measurement of a saddle for the cyclist is the saddles' width. Once the preferred saddle shape has been determined, the correct width needs to be and can now be determined. A saddle's width is measured at the widest point at the rear of the saddle. Most saddles of a specific model come in an availability of different common widths, typically 130 mm, 140 mm, 150 mm, 160 mm. Other widths are available in specialty saddles. For those saddles that are designated as Small (S), Medium (M), Large (L), etc., the measuring device can be easily used to measure the exact width in millimeters of these types of saddles as well.

The combination of the cyclist riding style and the cyclist riding position (both determined during the pre-interview process), IT bone width and saddle shape are all used to determine which saddle width and saddle shape is the best choice for the cyclist. FIG. 12 shows a curved top saddle being measured. FIG. 13 shows a flat top saddle being measured. FIG. 14 is a perspective view of FIG. 13 showing the relative flatness of the rear portion of the saddle.

Figure 16:
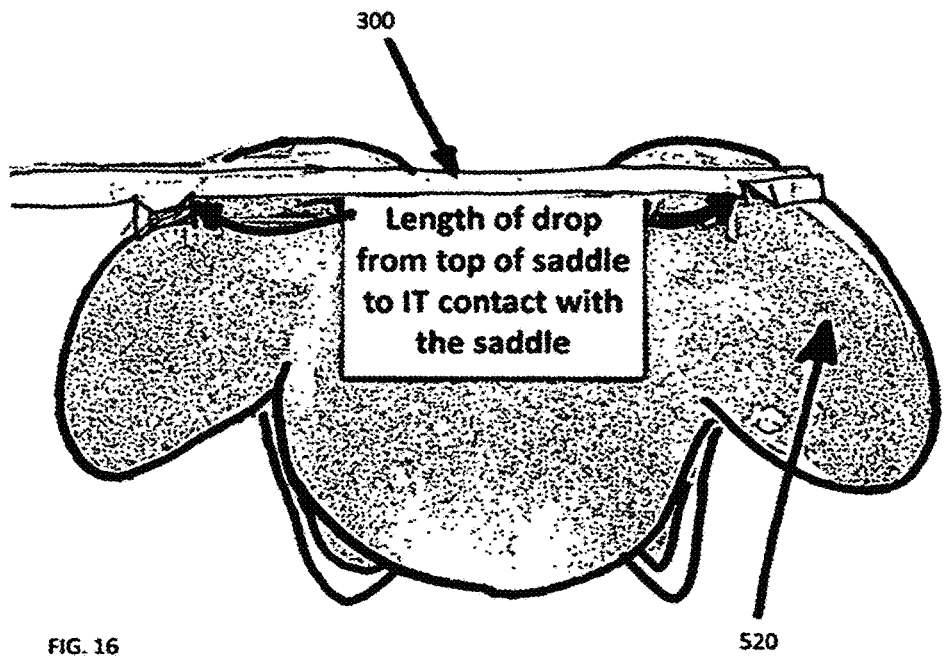
FIG. 16—is a front elevation view of one embodiment of a curved-top saddle showing the caliper gauge IT bone measuring tool set to measure distance from where the soft tissue sets on the saddle top to how much lower the IT bones sit on the saddle.

More specifically, a cyclist will want to go with the exact size as measured/indicated for a flat top saddle and one width size wider for a curved top saddle. This is easily determined by placing the measurement tool 300, FIGS. 15-16 flat side against the saddle to determine vertical drop from the top of the saddle to where the IT bones will contact the saddle. This can be clearly seen in FIGS. 15-16. FIG. 15 is a representation of a flat top saddle showing very little drop from the top of the saddle to where the IT bones will come into contact with the saddle while FIG. 16, a representation of a saddle with a very large curve shows a significant drop from the top of the saddle to where the IT bones will come into contact with the saddle. Specifically, a curved top saddle will curve away quickly from the center-line of the saddle so if the saddle is too narrow, the cyclists' IT bones will be either off the edge, or so low along the edge of the saddle that there will be no support for the cyclists' IT bones, therefore, all of the cyclists' weight will be on their soft tissue. FIG. 15 shows the measuring device set to an 80 mm IT bone width with virtually no vertical drop from the center flat part of the saddle to where the IT bones will contact the saddle. FIG. 16 shows a saddle with an aggressive curve, and, with the measuring device set to the same 80 mm, there is a much greater vertical drop from the top of the saddle to where the IT bones will come into contact with the saddle. In the case of the cyclist choosing a curved top saddle as depicted in FIG. 16, the cyclist will want to go one size width wider than if choosing a flatter top saddle as depicted in FIG. 15. This IT width measurement fitting system 100 and tool 300 FIG. 15, FIG. 16 easily shows this.

FIG. 17 depicts another embodiment of the fitting tool 100. The embodiment of FIG. 17 can be generally similar to any of the other embodiments of the fitting tool 100 disclosed herein. The fitting tool 100 of FIG. 17 includes a single impression pad 110. This can be used as an alternative to the dual impression pad design as depicted in FIG. 1. It is envisioned that this IT measurement system 100 FIG. 17, will be used by the fitter for standard saddles without holes or cutouts and that the dual-pad IT measurement system depicted as 100 FIG. 1 will be used for saddles with holes or cutouts.

Figure 18:
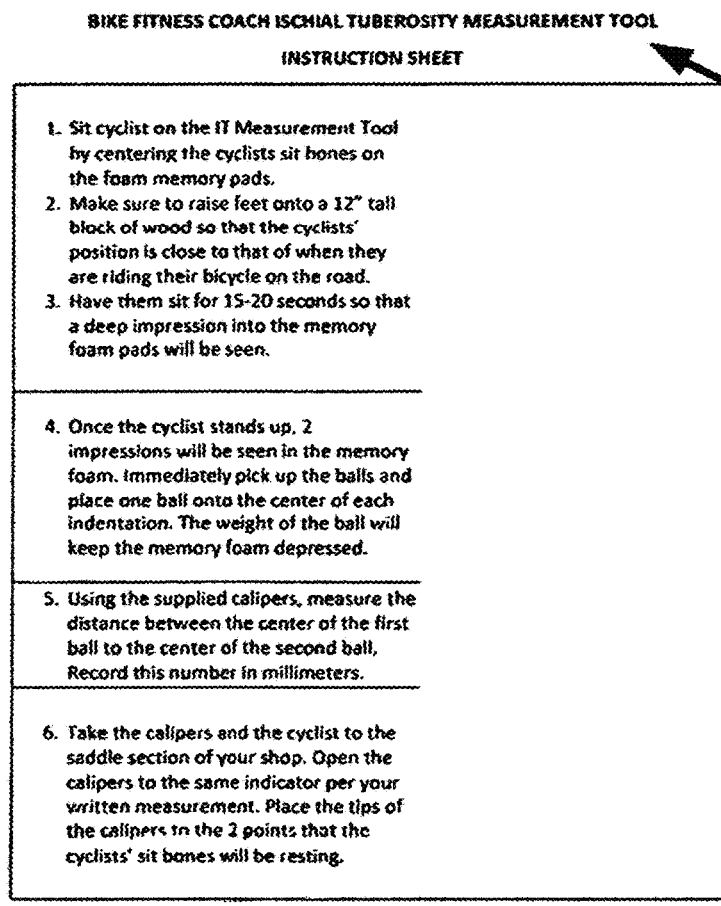
FIG. 18—is an elevation view showing the accompanying Instruction Sheet.

FIG. 18 depicts a step-by-step instruction sheet 600.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular embodiments described above, but should be determined only by a fair reading of these claims.

What is claimed:

1. A bicycle saddle fit system comprising a base, at least one impression pad of sufficient size to span the Ischial Tuberosity (IT) bones of a user and removably fastened to said base; said at least one impression pad being made of a material with sufficient shape memory to maintain impressions long enough to permit the measurement of a distance between impressions left by a user sitting and standing during the measurement process; a substrate layer extending laterally beyond the perimeter and securely fixed to the at least one impression pads; a set of ferrous metal balls that will self-level on the at least one impression pad, wherein said ferrous balls will be placed in the impressions left by the user in said impression pad; a detached measurement gauge comprising a scale used to measure from the center of each of said ferrous metal balls after each metal balls are placed on the at least one impression pads which will indicate the distance between the IT impressions of the cyclist previously seated on the at least one impression pads; wherein when the measurement gauge is placed over a saddle will clearly show the amount of drop from a level surface to the point of contact of the users' IT.

2. The fit system of claim 1, wherein a set of magnets can be attached to the fit system to keep ferrous balls stored in place.

3. The fit system of claim 1, wherein the measurement gauge comprises a detached and separate measuring device that can be taken over to a saddle to show exact placement of the cyclists' IT onto the saddle.

4. The fit system of claim 1, wherein the measurement gauge when placed over a saddle will clearly show the amount of drop from a level surface to the point of contact of the cyclists' IT.

5. The fit system of claim 1, further comprising a substrate layer underlying and fixed to the impression pad.

6. The fit system of claim 1, wherein it includes an exposed portion of the substrate layer which extends laterally beyond the perimeter of the impression pad.

7. The fit system of claim 1, wherein the impression pad comprises a layer of foam which is about 5-50 mm thick.

8. The fit system of claim 1, wherein it is comprised of 2 balls about 5-30 mm in diameter that will self-level into the depressions that are formed by the cyclists' IT bones into the impression pad substrate layer.

* * * * *